United States Patent
Mewissen et al.

(10) Patent No.: US 6,517,205 B2
(45) Date of Patent: Feb. 11, 2003

(54) APPARATUS FOR TREATMENT WITH LIGHT

(75) Inventors: Jan Alfons Catarina Mewissen, Drachten (NL); Henriet Jacqueline Corina Hinnen, Drachten (NL)

(73) Assignee: Koninklijke Philips Electronics N.V., Eindhoven (NL)

( * ) Notice: Subject to any disclaimer, the term of this patent is extended or adjusted under 35 U.S.C. 154(b) by 64 days.

(21) Appl. No.: 09/860,357

(22) Filed: May 18, 2001

(65) Prior Publication Data

US 2002/0015133 A1 Feb. 7, 2002

(30) Foreign Application Priority Data

May 19, 2000 (EP) .............................. 00201776

(51) Int. Cl.[7] .............. A61B 3/00; F21V 7/00; G01T 1/20
(52) U.S. Cl. ................ 351/203; 250/365; 250/504 R; 362/1
(58) Field of Search ................. 351/203; 250/365, 250/372, 461.1, 503.1, 504 R, 522.1; 362/1, 812

(56) References Cited

U.S. PATENT DOCUMENTS 5,426,879 A * 6/1995 Hecker ................... 40/427
6,271,528 B1 * 8/2001 Struye et al. ............ 250/484.5

FOREIGN PATENT DOCUMENTS

DE     4433291 A1    3/1996

* cited by examiner

Primary Examiner—Pamela Wilson
(74) Attorney, Agent, or Firm—Aaron Walker

(57) ABSTRACT

Apparatus (1) for treatment with light for personal care comprising a housing (2) with a light source, which housing (2) is covered with a wall (4) made from a translucent material, on which wall (4) a focusing area (5) is provided, to which focusing area (5) a user's eyes are mainly directed during use. On the wall (4), side areas (6) are provided adjacent said focusing area (5), and at least a portion of the wall (4) has a reference brightness during operation. Means (8) are provided in the apparatus (1) for varying a brightness of the focusing area (5) of the wall (4) during operation between the reference brightness and a minimum brightness which is lower than the reference brightness. In this way, the brightness of the focusing area (5) can be adjusted to a level which is low relative to the brightness of the side areas (6). A user thus experiences looking at the wall (4) during operation as more comfortable because he/she is not looking at a whole area of uniform brightness.

4 Claims, 3 Drawing Sheets

APPARATUS FOR TREATMENT WITH LIGHT

Figure 1:
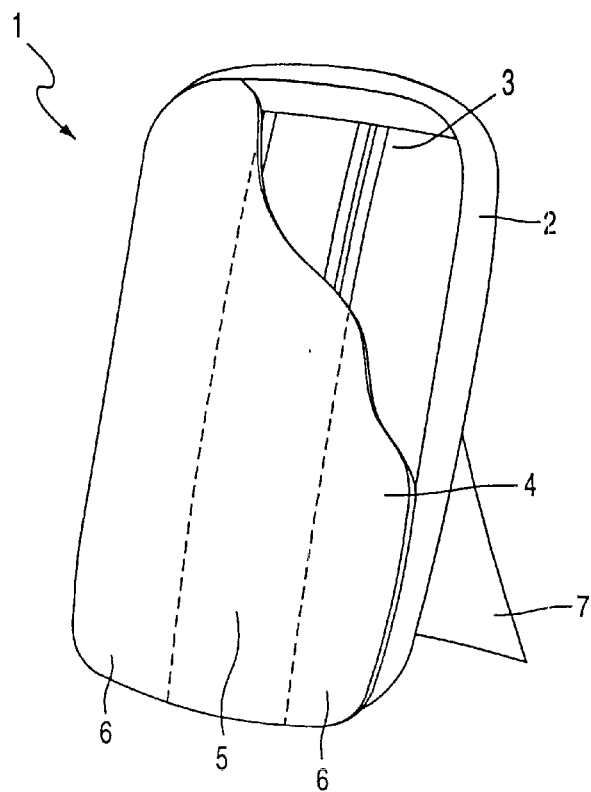

The invention relates to an apparatus for treatment with light for personal care, comprising a housing in which a light source is present and which is covered with a wall made from a translucent material, on which wall a focusing area is present to which a user's eyes are mainly directed, and on which wall side areas are present adjoining the focusing area such that at least a portion of the wall has a reference brightness during use.

A treatment with light contributes, for example, to combating a lack of energy related to the quantity of daylight. It is known that people experience a lack of energy when it is autumn or winter. This lack of energy was found to be related to the reduced quantity of daylight on an autumn or winter day compared with the quantity of daylight on a summer day. It was also found that this lack of energy can be combated in that the persons who are sensitive to this decrease in the quantity of daylight are regularly brought into the immediate vicinity of a light source which radiates artificial daylight with a high brightness.

An apparatus for treatment with light for personal care as described above is known from DE 44 33 291 A1.

The known apparatus comprises a housing with a wall made from a translucent material, i.e. consisting of a structured transparent synthetic resin material. A light source is furthermore present in the housing with lamps, said lamps being daylight fluorescent lamps. These lamps have a high brightness and are designed for the treatment of a lack of energy related to the quantity of daylight. The wall made from translucent material has a focusing area on which a user's eyes are mainly focused during use, and side areas adjoining the focusing area. During use, the user watches the wall transmitting the bright light emitted by the lamps during a certain time, which contributes to an improvement of his or her energy. It is a disadvantage of the known apparatus that the high brightness of the illuminated wall is sometimes experienced as unpleasant by the user, which detracts from the comfort of use.

It is an object of the invention to provide an apparatus of the kind mentioned in the opening paragraph which also achieves an effective treatment with light, but which has an improved comfort of use.

The above object is achieved with an apparatus according to the invention which is characterized in that a means is present for varying a brightness of the focusing area of the wall during use between the reference brightness and a minimum brightness which is lower than the reference brightness. The reference brightness of the wall during use is dependent on the type of light source used for the treatment. The reference brightness of the wall is determined by the luminous intensity of the light source when the apparatus is used for counteracting the lack of energy related to the quantity of daylight. It is possible through the measure mentioned above on the one hand to set the brightness of the focusing area comparatively low during use of the apparatus in relation to that of the side areas, which have the reference brightness. As a result, the side areas of the wall will have a brightness suitable for counteracting the lack of energy during use, and the quantity of light required for this counteracting can reach the user's eyes. The focusing area of the wall, furthermore, is present as a comparatively dark area between the brightly illuminated side areas in the field of view of the user who watches the focusing area on the wall during use. In this manner, counteracting of the lack of energy related to the quantity of daylight is still achieved, while watching the wall is pleasant for the user because he or she does not watch one area of uniform brightness. In addition, the user may thus adjust the brightness of the focusing area of the wall to suit his or her personal preference, so that a relation between the dark area and the bright areas on the wall is realized which is as pleasant as possible for him or her. All this benefits the comfort of use of the apparatus.

On the other hand, it is possible in this manner to give the apparatus an additional function. It becomes possible to use the apparatus as a lighting device in that the brightness of the focusing area is set such that it is equal to the brightness of the side areas. In fact, the wall thus forms a surface of uniformly distributed brightness, which is indeed favorable and desirable for lighting purposes and is not experienced as unpleasant by users, because the apparatus is not watched directly for a longer period.

An embodiment of an apparatus according to the invention is characterized in that the light source comprises lamps, and said means comprises a device for the displacement of at least one lamp from a first position, in which the relevant lamp is present adjacent the focusing area, into a second position, in which the relevant lamp is present adjacent one of the side areas. If the relevant lamp has been displaced in this manner from a position adjacent the focusing area into a position adjacent a side area by means of the device, a comparatively dark region will arise in the focusing area of the wall during use. The brightness of the focusing area is thus varied in a practical and effective manner, while the total light output of the apparatus does not change.

A further embodiment of an apparatus according to the invention is characterized in that said means comprises at least one reflector which is displaceable relative to the light source. The reflector is displaceable such that the light rays from the light source are reflected towards the focusing area and to the side areas by the reflector when the reflector is in a first position, and to the side areas when the reflector is in a second position. The focusing area is thus comparatively dark with the reflector in its second position. The brightness of the focusing area can be varied in that the reflector is adjusted to a position between the first and the second position, whereby the light rays are variably deflected. It can be realized by means of this device that a variable brightness of the focusing area of the wall is again easily achieved during use, while the total light output of the apparatus also remains the same.

A further embodiment of an apparatus according to the invention is characterized in that the light source comprises lamps, and said means comprises a dimming device for reducing the luminous intensity of at least one lamp present in the housing adjacent the focusing area of the wall during operation. The brightness of the focusing area can again be easily varied with respect to the reference brightness in this manner, while the construction of the apparatus is very simple.

Figure 2:
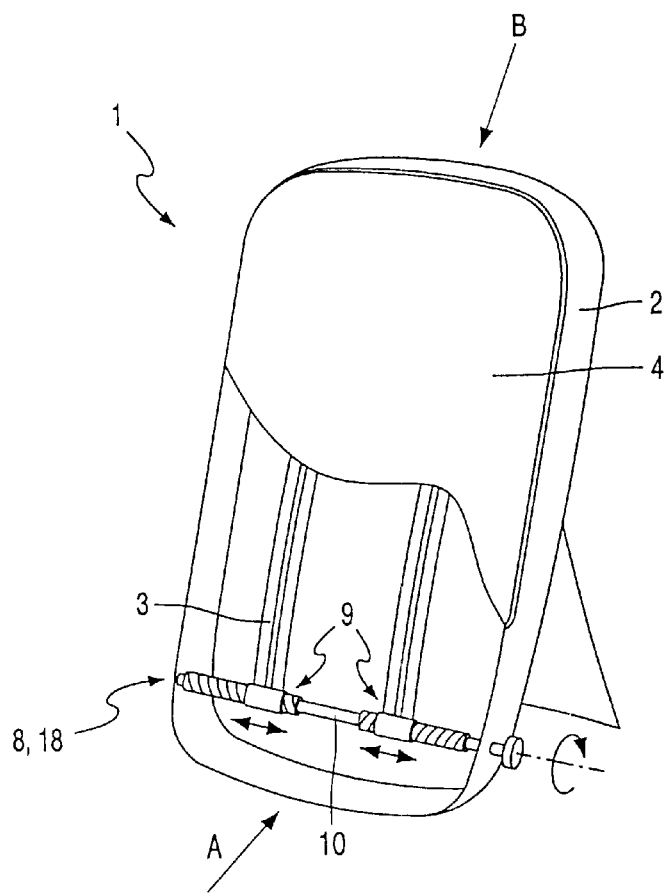
Figure 5:
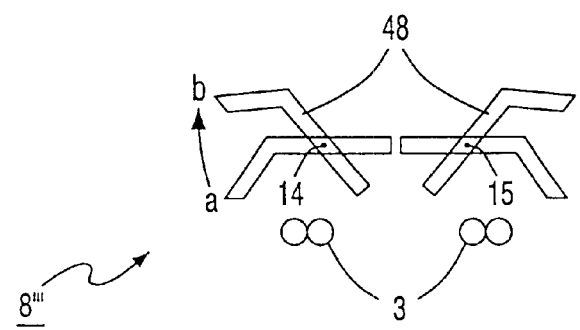
Figure 6:
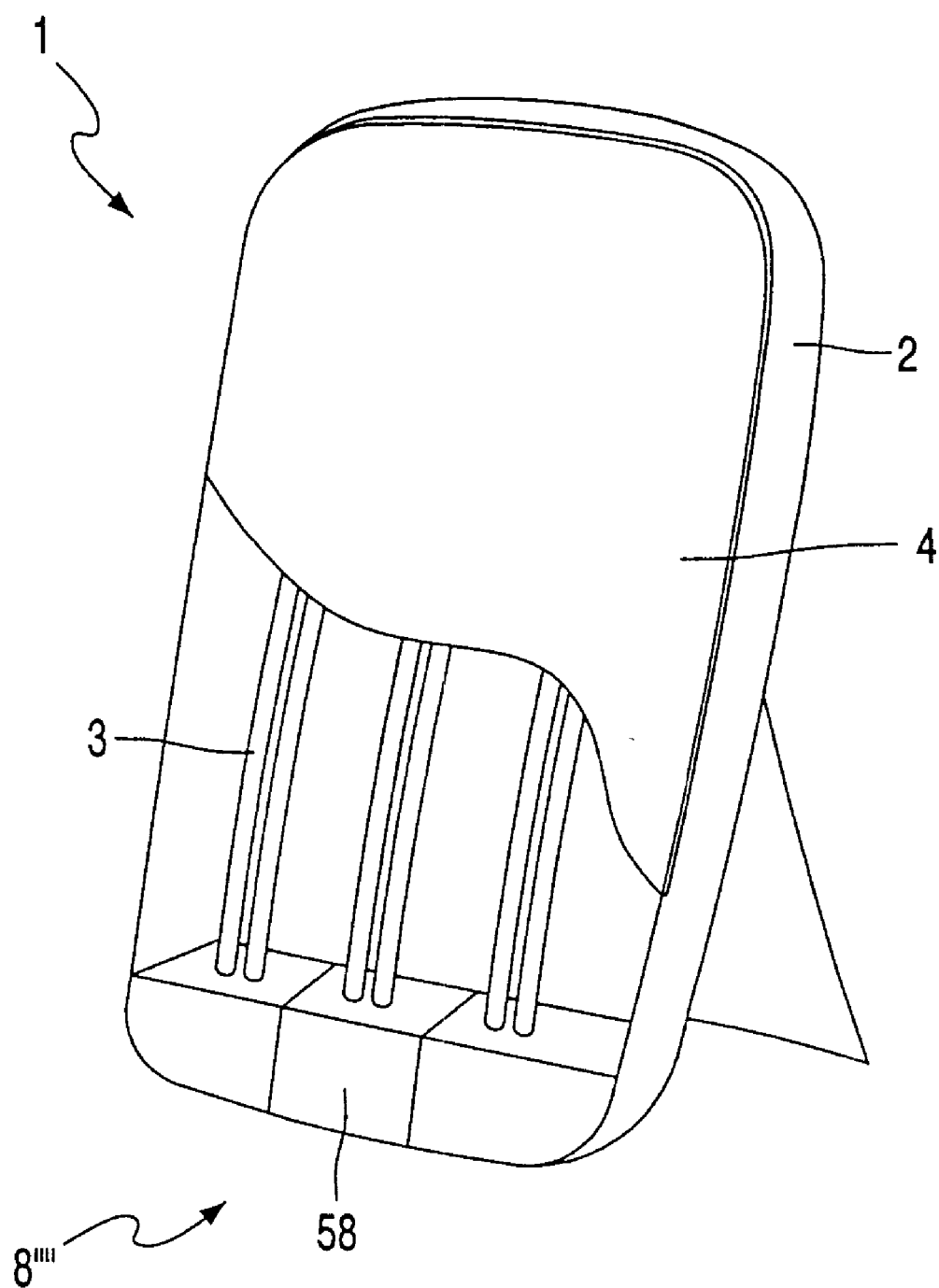

The apparatus according to the invention will be explained in more detail below with reference to the drawing, in which FIG. 1 shows a first embodiment of the apparatus according to the invention in perspective view, partly broken away, FIG. 2 shows the apparatus of FIG. 1 with another portion broken away, FIG. 3, viewed from a direction A indicated in FIG. 2, diagrammatically shows a means for varying a brightness of a focusing area of a wall of the apparatus during operation in a second embodiment of the apparatus according to the invention, FIG. 4, viewed from a direction B indicated in FIG. 2, diagrammatically shows a means for varying a brightness of a focusing area of a wall of the apparatus during operation in a third embodiment of the apparatus according to the invention, FIG. 5, viewed from the direction B indicated in FIG. 2, diagrammatically shows a means for varying a brightness of a focusing area of a wall of the apparatus during operation in a fourth embodiment of the apparatus according to the invention, and FIG. 6 shows a fifth embodiment of the apparatus according to the invention in perspective view, partly broken away.

FIG. 1 shows an apparatus 1 for the treatment with light for personal care according to the invention, comprising a housing 2 in which a light source is present with lamps 3, in this embodiment PL-L lamps suitable for counteracting a lack of energy related to the quantity of daylight. The apparatus 1 in this embodiment also comprises a stand 7. The apparatus 1 further comprises a supply unit and electronics, which are not pictured here. The housing 2 is covered with a wall 4 made from a translucent material, in this embodiment a wall of synthetic resin such as, for example, acryl. A focusing area 5 on which a user's eyes are mainly focused is present on the wall 4. The focusing area in this embodiment lies oriented as a vertical band in the central portion of the wall, as seen from the operational position of the apparatus. Side areas 6 are furthermore present on the wall so as to adjoin the focusing area, on either side of the focusing area 5 in this embodiment. At least a portion of the wall has a reference brightness during use. The maximum brightness of the wall in this embodiment is approximately 10,000 candelas per $m^2$.

As is apparent from FIG. 2, a means 8 is present in the apparatus 1 for varying a brightness of the focusing area 5 of the wall 2 during use between the reference brightness and a minimum brightness which is lower than the reference brightness. This means 8 in this embodiment comprises a threaded device 18 which is present in the housing adjacent the ends 9 of the lamps 3. The threaded device 18 comprises a spindle 10 with two screw threads which have mutually opposed pitches. The two screw threads are in engagement with two nuts which are each fastened to one of the lamps. Furthermore, the threaded device 18 comprises a rotary knob which projects outside the housing 2. A rotary movement given to the rotary knob 11 can thus be converted into a translatory movement of the lamps 3 in opposite directions relative to one another and parallel to the spindle 10. Upon rotation of the rotary knob 11 in a first direction, no lamp will be present any more adjacent the focusing area 5 in the housing 2, so that this focusing area 5 will have a comparatively low brightness compared with the side areas 6 of higher brightness during use. A rotary movement in a direction opposed to the former given to the rotary knob 11 will be converted in a movement of the lamps 3 towards one another and parallel to the spindle 10. The lamps 3 will thus be present adjacent the focusing area 5 in the housing 2, and the focusing area 5 will have a brightness corresponding to the brightness of the side areas 6 during use.

Figure 3:
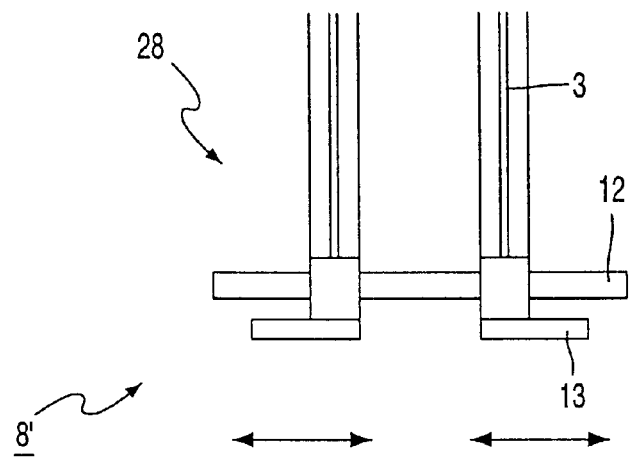

FIG. 3 shows an embodiment of the apparatus according to the invention which is provided with a means 8' with which the lamps can also be displaced in opposite directions. The means 8' in this embodiment is a sliding device 28, the lamps 3 being supported with sliding possibility along a shaft 12. The lamps can be shifted relative to one another along the shaft 12 by means of handles 13, so that the lamps can be moved away from and towards one another along the shaft 12. This achieves that the focusing area 5 may have a lower brightness than the side areas 6 and a brightness equal to that of the side areas 6, respectively, during operation.

Figure 4:
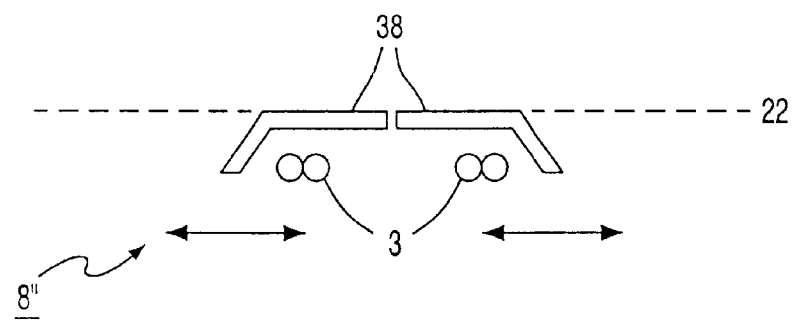

FIG. 4 shows an embodiment of the apparatus according to the invention which is provided with a means 8" for varying a brightness of the focusing area 5 of the wall 2 during use between the reference brightness and a minimum brightness lower than the reference brightness. The means 8" in this embodiment comprises a reflector 38 which is displaceable relative to the lamps 3. The reflector 38 in this embodiment is adjustable relative to the lamps in that the reflector comprises two parts which can be shifted parallel to an axis 22 in a manner comparable to the displacement of the lamps in the preceding embodiment. When the parts have been moved away from one another along the axis 22, the light rays from the lamps 3 are reflected towards the side areas 6 and not to the focusing area 5 on the wall 2. As a result, this focusing area 5 will have a comparatively low brightness in relation to the side areas 6 of high brightness during operation. When the parts have been moved towards one another along the axis 22, the light rays from the lamps 3 are reflected in the direction of the focusing area 5 on the wall 2 during operation, so that the focusing area 5 has a brightness corresponding to the brightness of the side areas 6 during operation.

FIG. 5 shows an embodiment of the apparatus according to the invention which is provided with a means 8''', which again comprises a reflector which is displaceable relative to the lamps. In this embodiment, the reflector 48 is displaceable relative to the lamps 3 in that it is journaled with rotation possibility about axes 14 and 15 relative to the lamps 3. In a first position a of the reflector 48, the light rays from the lamps 3 are reflected towards the focusing area 5 on the wall 2 during use, so that the focusing area 5 has a brightness corresponding to the brightness of the side areas 6 during use. If the reflector 48 is rotated into a second position b and light rays from the lamps 3 are reflected thereby, the light rays will pass through the side areas 6 only and not through the focusing area 5 of the lamp. This focusing area 5 is comparatively dark in this manner. The brightness of the focusing area can be varied through adjustment of the position of the reflector. A variation of a brightness during use of the focusing area 5 between the reference brightness and a minimum brightness lower than the reference brightness can thus be achieved in a simple manner.

FIG. 6 shows an embodiment of the apparatus according to the invention which is provided with a means 8"" for varying a brightness of the focusing area 5 of the wall 2 between the reference brightness and a minimum brightness lower than the reference brightness during operation. In this embodiment, the means 8"" comprises an electric dimming device 58 for reducing the luminous intensity of at least one lamp present in the housing 2 adjacent the focusing area 5 of the wall 4 during operation. Again, the brightness of the focusing area 5 can be easily varied in this manner, while the mechanical construction of the apparatus is very simple.

It is noted that the invention also relates to apparatuses with a UV light source for tanning the skin and for the treatment of certain skin conditions. The maximum brightness of the wall in this embodiment is approximately 2000 candela per $m^2$.

It is further noted that it is also possible for the focusing area to have a different orientation on the wall. The lamps may be present in the apparatus in horizontal position and may be movable away from and towards one another. In that case, the focusing area would be oriented as a horizontal band on the wall, viewed from the operational position of the apparatus, with the "side faces" now at the upper and lower sides.

It is further noted that alternative means may be used for varying the brightness of the focusing area of the wall between the reference brightness and a minimum brightness lower than the reference brightness during operation instead of the embodiments mentioned above. It is possible, for example, to use a detachable diffuse plate or sticker on the wall. This offers a wide range of choices as regards the shape and size of the focusing area. A focusing area may thus be realized which is in accordance with a user's preference.

What is claimed is:

1. An apparatus (1) for treatment with light for personal care, which apparatus comprises
   a housing (2) in which a light source is present,
   said housing (2) being covered with a wall (4) manufactured from a translucent material,
   on which wall (4) a focusing area (5) is present to which a user's eyes are mainly directed during use and on which wall (4) side areas (6) adjoining the focusing area (5) are present,
   at least a portion of the wall (4) having a reference brightness during operation, characterized in that a means (8) is present for varying a brightness of the focusing area (5) of the wall (4) during use between the reference brightness and a minimum brightness which is lower than the reference brightness.

2. An apparatus as claimed in claim 1, characterized in that the light source comprises lamps (3), and said means (8) comprises a device (18, 28) for the displacement of at least one lamp from a first position, in which the relevant lamp is present adjacent the focusing area (5), into a second position, in which the relevant lamp is present adjacent one of the side areas (6).

3. An apparatus as claimed in claim 1, characterized in that said means (8) comprises at least one reflector (38, 48) which is displaceable relative to the light source.

4. An apparatus as claimed in claim 1, characterized in that the light source comprises lamps (3), and said means comprises a dimming device (58) for reducing the luminous intensity of at least one lamp present in the housing (2) adjacent the focusing area (5) of the wall (4) during operation.

* * * * *